(12) United States Patent
Winkler, Sr.

(10) Patent No.: US 12,324,726 B2
(45) Date of Patent: Jun. 10, 2025

(54) WOUND DRESSING GARMENTS, KITS, SYSTEMS, AND METHODS

(71) Applicant: Compression Dynamics, LLC, Omaha, NE (US)

(72) Inventor: Martin J. Winkler, Sr., Omaha, NE (US)

(73) Assignee: COMPRESSION DYNAMICS, LLC, Omaha, NE (US)

( * ) Notice: Subject to any disclaimer, the term of this patent is extended or adjusted under 35 U.S.C. 154(b) by 161 days.

(21) Appl. No.: 17/300,127

(22) Filed: Mar. 18, 2021

(65) Prior Publication Data
US 2021/0290443 A1    Sep. 23, 2021

Related U.S. Application Data

(60) Provisional application No. 62/991,155, filed on Mar. 18, 2020.

(51) Int. Cl.
*A61F 13/02* (2024.01)
*A61F 13/05* (2024.01)
(Continued)

(52) U.S. Cl.
CPC .............. *A61F 13/05* (2024.01); *A61F 13/08* (2013.01); *A61F 13/10* (2013.01); *A61L 15/22* (2013.01);
(Continued)

(58) Field of Classification Search
CPC ...... A61F 13/0216; A61F 13/08; A61F 13/10; A61F 2013/00319; A61F 2013/00323;
(Continued)

(56) References Cited

U.S. PATENT DOCUMENTS

| 2,053,123 A | 9/1936 | Alles |
|---|---|---|
| 3,306,288 A | 2/1967 | Benjamin et al. |

(Continued)

FOREIGN PATENT DOCUMENTS

| WO | 2007140235 A2 | 12/2007 |
|---|---|---|
| WO | 2014144790 A1 | 9/2014 |
| WO | 2020014310 A1 | 1/2020 |

OTHER PUBLICATIONS

Notification of Transmittal of the InternationalSearch Report and the Written Opinion of the International Searching Authority, or the Declaration dated Sep. 8, 2021 for App. No. PCT/US21/10011.

*Primary Examiner* — Rebecca E Eisenberg
*Assistant Examiner* — Rachel O'Connell
(74) *Attorney, Agent, or Firm* — Daniel J. Honz; Advent, LLP (57) ABSTRACT

Wound therapy compression garments and layered dressing kits are described. In an aspect, a kit includes a compression garment and one or more fenestrated dressing layers. The compression garment includes a plurality of hydrophobic longitudinal wales arranged to form a fabric with a plurality of hydrophilic transverse elastomeric threads under variable tension connecting adjacent ones of the hydrophobic longitudinal wales in such way as to deliver elastic compression at a wound site. The hydrophobic longitudinal wales and the hydrophilic transverse elastomeric threads cooperate to generate hydrostatic pressure for transporting fluid away from the wound site. The fenestrated dressing layer(s) is configured to form a textured interface with the compression garment and increase movement of fluid away from the wound site.

18 Claims, 7 Drawing Sheets

(51) Int. Cl.
   *A61F 13/08*    (2006.01)
   *A61F 13/10*    (2006.01)
   *A61L 15/22*    (2006.01)
   *A61L 15/42*    (2006.01)
   *A61M 1/00*     (2006.01)
   *A61F 13/00*    (2006.01)

(52) U.S. Cl.
   CPC .......... *A61L 15/425* (2013.01); *A61M 1/912* (2021.05); *A61F 2013/00319* (2013.01); *A61F 2013/00323* (2013.01); *A61L 2300/404* (2013.01)

(58) Field of Classification Search
   CPC ...... A61M 1/912; A61L 15/22; A61L 15/425; A61L 2300/404
   See application file for complete search history.

(56) References Cited

U.S. PATENT DOCUMENTS

| | | |
   |---|---|---|
   | 3,409,008 A | 11/1968 | Mortensen et al. |
   | 3,570,482 A | 3/1971 | Emoto et al. |
   | 3,728,875 A | 4/1973 | Knohl et al. |
   | 3,747,374 A | 7/1973 | Meyer et al. |
   | 4,015,448 A | 4/1977 | Knohl |
   | 4,377,160 A | 3/1983 | Romaine |
   | 4,424,808 A | 1/1984 | Schaefer et al. |
   | 4,520,635 A | 6/1985 | Shields et al. |
   | 4,657,003 A | 4/1987 | Wirtz |
   | 4,832,010 A | 5/1989 | Lerman |
   | 4,841,747 A | 6/1989 | Frenzel et al. |
   | 5,257,956 A | 11/1993 | Ewen |
   | 5,344,406 A | 9/1994 | Spooner |
   | 5,695,452 A | 12/1997 | Grim et al. |
   | 5,735,807 A | 4/1998 | Cropper |
   | 6,311,334 B1 | 11/2001 | Reinhardt et al. |
   | 6,435,221 B1 | 8/2002 | Waldrop et al. |
   | 7,867,185 B2 | 1/2011 | Lipshaw |
   | 8,034,013 B2 | 10/2011 | Winkler |
   | 8,641,653 B2 | 2/2014 | Winkler |
   | 9,387,125 B1 * | 7/2016 | Duda .................... A61F 13/066 |
   | 2006/0189913 A1 | 8/2006 | Winkler |
   | 2007/0179421 A1 | 8/2007 | Farrow |
   | 2011/0282309 A1 * | 11/2011 | Adie ..................... A61F 13/022 |
   | | | 604/319 |
   | 2013/0014544 A1 * | 1/2013 | Winkler .................. D04B 1/24 |
   | | | 66/147 |
   | 2013/0096478 A1 | 4/2013 | Cureton et al. |
   | 2014/0148742 A1 | 5/2014 | Winkler |
   | 2015/0150710 A1 | 6/2015 | Evans |
   | 2015/0190559 A1 | 7/2015 | Locke et al. |
   | 2019/0224376 A1 * | 7/2019 | Jessop .................. A61L 27/362 |
   | 2019/0262181 A1 * | 8/2019 | Long .................... A61M 1/915 |
   | 2020/0000643 A1 * | 1/2020 | Locke ............... A61F 13/00063 |
   | 2020/0009611 A1 * | 1/2020 | Voskian ................ A01N 59/16 |
   | 2020/0032435 A1 * | 1/2020 | Morishita ......... A61F 13/49011 |
   | 2020/0188183 A1 * | 6/2020 | Hamerslagh ............ A61L 15/60 |

* cited by examiner

WOUND DRESSING GARMENTS, KITS, SYSTEMS, AND METHODS

CROSS-REFERENCE TO RELATED APPLICATIONS

The present application claims the benefit under 35 U.S.C. § 119(e) of U.S. Provisional Application Ser. No. 62/991,155, filed Mar. 18, 2020, and titled "TEXTILE SYSTEM FOR REAL TIME CONTROL OF COMORBID: INFECTION, BACTERIAL BIOFILM, EXUDATE, MACERATION, CELL DYSTAXIS, AND EXCESSIVE INFLAMMATORY MEDIATORS COMPLICATING ELASTIC COMPRESSION THERAPY," which is herein incorporated by reference in its entirety.

BACKGROUND

Wound care or wound therapy involves the diagnosis, treatment, and management of a wound to promote healing and reduce the occurrence of infection.

SUMMARY

Wound dressing garments, kits, systems, and methods are described herein. In an aspect, a kit includes, but is not limited to, a compression garment and one or more fenestrated dressing layers. The compression garment includes a plurality of hydrophobic longitudinal wales and a plurality of hydrophilic transverse elastomeric threads under variable tension. The plurality of hydrophobic longitudinal wales includes a first set of wales and an alternating second set of wales. The first set of wales are loaded with a first metal and the second alternating second set of wales are loaded with a second metal, wherein the first set of wales and the alternating second set of wales cooperate to generate an electrochemical current. The plurality of hydrophilic transverse elastomeric threads is arranged to form a fabric with the plurality of hydrophobic longitudinal fuzzy wales by connecting adjacent ones of the plurality of hydrophobic longitudinal fuzzy wales in such way as to deliver elastic compression at a wound site, wherein the hydrophobic longitudinal fuzzy wales and the hydrophilic transverse elastomeric threads cooperate to generate hydrostatic pressure for transporting fluid away from the wound site. The fenestrated dressing layer(s) is configured to form a textured interface with the compression garment and increase movement of fluid away from the wound site.

In an aspect, a kit includes a compression garment and one or more fenestrated dressing layers. The compression garment includes a plurality of hydrophobic longitudinal wales arranged to form a fabric with a plurality of hydrophilic transverse elastomeric threads under variable tension connecting adjacent ones of the hydrophobic longitudinal wales in such way as to deliver elastic compression at a wound site. The hydrophobic longitudinal wales and the hydrophilic transverse elastomeric threads cooperate to generate hydrostatic pressure for transporting fluid away from the wound site. The fenestrated dressing layer(s) is configured to form a textured interface with the compression garment and increase movement of fluid away from the wound site.

In an aspect, a wound dressing compression garment includes a plurality of hydrophobic longitudinal fuzzy wales and a plurality of hydrophobic transverse elastomeric threads under variable tension. The plurality of hydrophobic longitudinal fuzzy wales includes a first set of wales and an alternating second set of wales. The first set of wales are loaded with a first metal, and the alternating second set of wales are loaded with a second metal, wherein the first set of wales and the alternating second set of wales cooperate to generate an electrochemical current. The plurality of hydrophilic transverse elastomeric threads is arranged to form a fabric with the plurality of hydrophobic longitudinal fuzzy wales by connecting adjacent ones of the plurality of hydrophobic longitudinal fuzzy wales in such way as to deliver elastic compression at a wound site, wherein hydrophobic longitudinal fuzzy wales and the hydrophilic transverse elastomeric threads cooperate to generate hydrostatic pressure that transports fluid away from the wound site.

This Summary is provided to introduce a selection of concepts in a simplified form that are further described below in the Detailed Description. This Summary is not intended to identify key features or essential features of the claimed subject matter, nor is it intended to be used as an aid in determining the scope of the claimed subject matter.

DRAWINGS

The Detailed Description is described with reference to the accompanying figures. The use of the same reference numbers in different instances in the description and the figures may indicate similar or identical items.

DETAILED DESCRIPTION

Overview

Wound care and therapy are important for avoiding serious complications. Without proper care, a wound can turn into serious infections such as cellulitis or sepsis. Historically, difficult wounds have often been treated using negative pressure wound therapy (NPWT), otherwise known as vacuum-assisted closure (VAC). NPWT involves providing a vacuum in the space above the wound to promote healing. NPWT systems generally includes a foam layer applied directly to the wound, an adhesive film which covers the foam and seals the wound, and a drainage tube leading from under the adhesive film and connecting to a portable vacuum pump. The vacuum pump removes air pressure over the wound, either constantly or in cycles.

While NPWT treatments may offer therapeutic benefits over traditional gauze dressings or bandages, NPWT systems have several disadvantages. First, NPWT can increase the risk of infection. Because wound exudate is collected in the foam layer, NPWT requires frequent dressing changes in order to prevent infection. Dressings must be changed every 24 to 72 hours. Such frequent dressing changes may require frequent clinic visits, and can be cumbersome and painful for the patient. Additionally, maintaining an airtight seal may be difficult for some wound types (e.g., highly exudating wounds, irregular shaped wounds, wounds in close proximity to other structures, etc.). Loss of the airtight seal can cause extravasation of fluid resulting in periwound maceration and increasing the risk of infection. Second, the NPWT treatments themselves often require the patient to be connected to the vacuum pump for at least 22 hours per day, and may require the patient to remain stationary while the pump is connected. Alternatively, the patient may be required to carry a portable pump at all times. NPWT therapy for large or severe wounds may require in-patient treatment and may require the patient to be non-ambulatory, increasing the risk of complications. Further the required vacuum pump, dressings, and associated health care services may be cost-prohibitive. Last, NPWT can result in injury to the skin surrounding the wound and/or pressure necrosis from the drainage tubing.

Wounds treated with traditional dressings may also require extensive care that can be disruptive for the patient. Venous leg ulcers (VLUs), for example, represent 70% of ambulatory wounds treated in U.S. wound clinics. VLUs treated with traditional dressings require, on average, 30 weeks of once or twice weekly compression changes. Additionally, wounds like VLUs may present with comorbid conditions (e.g., edema, chronic bacterial biofilms, moisture-associated skin damage, etc.) that are difficult to manage or may be exacerbated by traditional dressings or NPWT.

Accordingly, the present disclosure is directed, at least in part, to wound dressing kits, systems, and methods. In an aspect, a wound dressing kit includes a compression garment and at least one fenestrated dressing layer. The compression garment includes a plurality of hydrophobic fuzzy wales arranged to form a fabric with a plurality of hydrophilic transverse elastomeric threads connecting adjust wales. The hydrophilic transverse elastomeric threads are configured to be under variable tension to deliver elastic compression to the wound site, and the hydrophobic wales and hydrophilic elastomeric threads cooperate to generate hydrostatic pressure for transporting different types of fluids (e.g., drainage, exudate, venous fluid, lymphatic fluid, etc.) away from the wound site. In some aspects, alternating wales may be loaded and/or coated with alternating metals to generate an electrochemical current and provide an antimicrobial effect. The fenestrated dressing layer(s) form a textured interface with the compression garment to increase movement of fluid away from the wound site. Because the textured interface formed between the compression garment and the fenestrated dressing layer(s) effectively transports fluid away from the wound site, the risk of infection is decreased in significantly less frequent dressing changes are required than when using NPWT therapy or traditional dressings (e.g., gauze, bandages, etc.). Additionally, because the dressing kit may be implemented without the use of pumps or other mechanical devices, the patient can remain fully ambulatory and costs can be substantially reduced.

Example Implementations

Referring generally to FIGS. 1A through 6, layered wound dressing kits, garments, systems, and methods are described. In embodiments, a wound dressing kit 100 includes a compression dressing or garment (e.g., compression garment 102) and a fenestrated dressing layer 104.

In embodiments, the compression garment 102 and the fenestrated dressing layer 104 are applied over a wound 106, for example, on an extremity 108 such as an arm or a leg (e.g., as described with reference to FIGS. 1A through 3). In some embodiments, the compression garment 102 is in direct contact with the surface of the wound 106 and the surrounding skin. The fenestrated dressing layer 104 is applied over the compression garment 102 (e.g., as described with reference to FIG. 2). In some embodiments, additional dressing layers (e.g., dressing layer 110; dressing layer 112) may be applied over the fenestrated dressing layer 104 (e.g., as described with reference to FIG. 3). For example, different types of therapeutic dressing layers may be combined to enhance wound drainage and/or antimicrobial properties of the kit 100. The properties of the compression garment 102 and each dressing layer 104, 110, 112 are described further herein.

Figure 4:
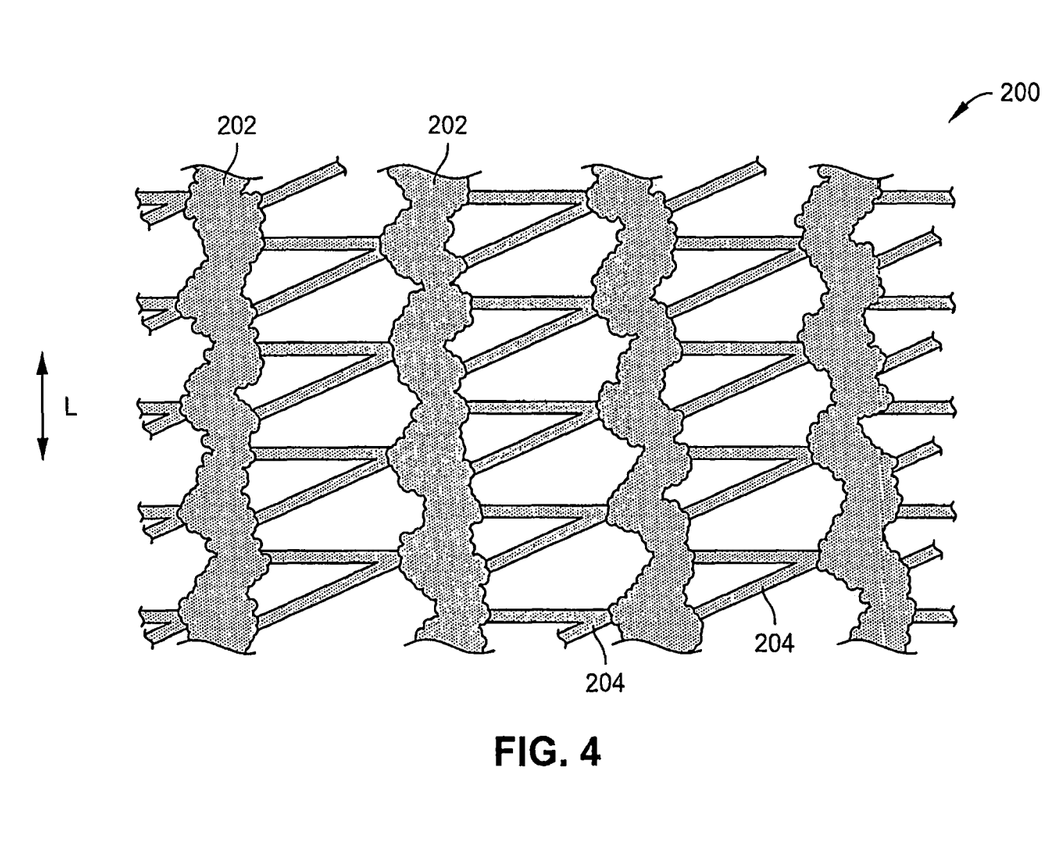
FIG. 4 is a plan view illustrating a fabric constructed in accordance with embodiments of the present disclosure, the fabric shown in a stretched state.

As shown in FIG. 4, the graduated compression garment 102 is formed from a fabric 200 that includes a plurality of primary or longitudinal wales 202 and a plurality of secondary, lateral or connective wales (e.g., transverse elastomeric threads 204). The primary wales 202 are arranged to be substantially parallel with a longitude L of the compression garment 102. The secondary transverse elastomeric threads 204 extend between and connect adjacent primary wales 202, to be further described. The secondary transverse elastomeric threads 204 are arranged to be secondary to the longitude L. It can be seen that, in some embodiments shown in the figures (e.g., as described with reference to FIG. 4), the secondary transverse elastomeric threads 204 are arranged at an angle other than about 90 degrees to the longitude L.

The fabric 200 can be knitted using a criss-crossing lateral stitch on a warp knitting machine. For instance, at least a portion of the plurality of substantially parallel primary wales 202 and the plurality of secondary transverse elastomeric threads 204 may be formed from a criss-crossing lateral stitch on a warp knitting machine to form the plurality of substantially parallel primary wales 202 and the plurality of secondary transverse elastomeric threads 204. In some embodiments, the fabric 200 may be arranged in a tubular form. In a specific embodiment, a tube of fabric 200 can include 60 continuous longitudinal wales 202 connected by a plurality of secondary or lateral wales 204. In some embodiments, a six-course repeat chain stitch is used. In such embodiments, when a tube of fabric 200 is stretched radially about any length of the fabric 200, the longitudinal wales 202 maintain their longitudinal orientation with respect to the overall tube of fabric 200.

In some embodiments, the primary or longitudinal wales 202 are formed from a hydrophobic polymer such as polyester, acrylic, and modacrylic, and so forth. Alternatively or in addition, a hydrophobic wale may be formed from an otherwise hydrophilic fiber by applying a hydrophobic finish (e.g., tetrabutyltitanate, octadecylamine, etc.) to the fiber. In a specific embodiment, the primary or longitudinal wales 202 are formed from a standard 3 ply 70 nylon wale having mild longitudinal recovery. In such embodiments, the nylon may be treated with a hydrophobic finish such as tetrabutyltitanate, octadecylamine, or the like to produce a hydrophobic nylon fiber. One or more individual longitudinal wales 202 of the plurality of longitudinal wales 202 may be formed from medical grade nylon knitted wales 202 arranged to form a fabric cylinder having a length and generally parallel to the length. The longitudinal wale material may comprise a plurality of light or fine fibers surrounding a core fiber. The plurality of light or fine fibers may produce a substantially fuzzy effect. The longitudinal wale 202 is capable of being stretched between a first un-stretched length and a second or stretched position with a fully stretched length being approximately 350% longer than the unstretched length. Specifically, in a stretched state, (e.g., when deployed on a human extremity or torso of proper size), the longitudinal wales 202 may be spaced with a ratio of about four wale diameters between one another and remain generally parallel to the length.

In some embodiments, the secondary transverse elastomeric threads 204 are formed from a hydrophilic polymer such as nylon, cotton, linen, and so forth. Alternatively or in addition, a hydrophilic thread may be formed from an otherwise hydrophobic fiber by applying a hydrophilic finish to the fiber. In a specific embodiment, the secondary transverse elastomeric threads 204 generate elastic compression in a starched state and may be formed from a polymer containing polyurethane such as commercially available spandex products. In such embodiments, the polyurethane polymer may be treated with a hydrophilic finish such as polyethylene glycol, aminosilicone, or the like, produce a fiber that is at least somewhat hydrophilic. It is important to note that the diameter of each longitudinal wale 202 is significantly larger than the diameter of each secondary thread 204. In specific embodiments, the diameter of the longitudinal wale 202 is approximately 11 times larger than the diameter of the secondary elastomeric thread 204. The plurality of elastomeric threads 204 may be elastomeric (e.g., spandex) or like elastic material and may connect adjacent longitudinal to form a fabric cylinder of longitudinal fuzzy wales 202 equally spaced about a length of the longitudinal wale 202.

While fabrics 200 having hydrophobic wales 202 and hydrophilic elastomeric threads 202 are described herein, the compression garment 102 is not limited to such configurations. Alternatively, the fabric 200 may be formed to have hydrophilic wales and hydrophobic elastomeric threads. It is further contemplated that substantially the entirety of the fabric 200 may be formed from either a hydrophobic or a hydrophilic material.

When a patient dons the compression garment 102 (e.g., as described with reference to FIGS. 1A through 3), the fabric 200 stretches creating space between adjacent longitudinal wales 202. Because of the elastic nature of the lateral threads 204, each longitudinal wale 202 exerts a compression force on the skin or surface of the patient's limb, only at the point of contact between the longitudinal wale 202 and the skin. The "point of contact" is a line of contact between the wale 202 and the wound surface, about the length of the longitudinal wale 202. Because of the disparity in the size of diameter of the primary wale 202 and the secondary elastomeric threads 204, the secondary, or lateral wales 204, do not exert any pressure directly on the wound or the limb in comparison to the pressure exerted by the longitudinal wales 202. Such embodiments can have at least two effects. First, the construction of the fabric 202 can reduce or eliminate tourniquet effects obstructing the arterial, venous, and lymphatic vessels. Second, because in cross section, the longitudinal or linear compression exerted by the longitudinal wale 202 is felt by the wound and limb at only discreet points, it has been found that patients are much better able to tolerate higher compression forces. This, in turn, allows compression garments 102 constructed of fabric 202 according to the present disclosure to utilize greater pressures sufficient to assist the deeper popliteal vein in removing fluid from the affected area (e.g., the wound).

While the compression garment 102 is shown as a tubular garment worn on the arm, the disclosure is not limited to such configurations. It is contemplated that the fabric 200 of the present disclosure may be used to create a tubular stocking to assist in treating the feet, ankles, or any portion of the legs. The fabric 200 may also be used to form a sleeve for treating the knee or elbow area; or the fabric 200 may be used to form a closed end tube for treating wounds in amputation situations. It is further contemplated that the fabric 200 may be used to form a pair of shorts extending down all or a portion of the thighs or a pair of tights extending down the entirety of the legs, or a shirt covering all or a portion of the torso.

In embodiments, the primary or longitudinal wale 202 alone is essentially in contact with the skin. While the lateral elastomeric threads 204 may occasionally come into contact with the skin, the lateral threads 204 do not exert any effective pressure on the extremity. The primary wales 202 have a soft or fuzzy outer surface. This fuzzy surface molds to the micro geography of the wound surface and "stents" the surrounding skin. Skin stenting will be further discussed below. The longitudinal fuzzy wale 202 stents the skin holding the wale 202 in place over a small strip of skin cells. The longitudinal wales 202 do not move relative to furrows 114 of skin formed beneath the longitudinal wales 202, even with motion of the extremity. This prevents shearing injuries to the skin.

The longitudinal fuzzy wale 202 may also provide both insulation and cooling of the wound surface and surrounding skin. For instance, the plurality of substantially parallel primary wales 202 may be formed from a material capable of raising the temperature of a region of the wound surface or skin in contact with the plurality of substantially parallel primary wales 202. In some instances, the longitudinal wale 202 insulates the skin and generally raises the skin temperature one to three degrees F. Elevating the skin temperature slightly can significantly increase blood flow to the area. Therefore, a compression garment 102 according the present disclosure can improve skin perfusion by warming the skin. Alternatively or additionally, the compression garment may be cooling in warm environments because, as described below, as much as 75% of the skin is open to allow heat to radiate, as well as breathable to allow sweat to evaporate from exposed skin.

Figure 1A:
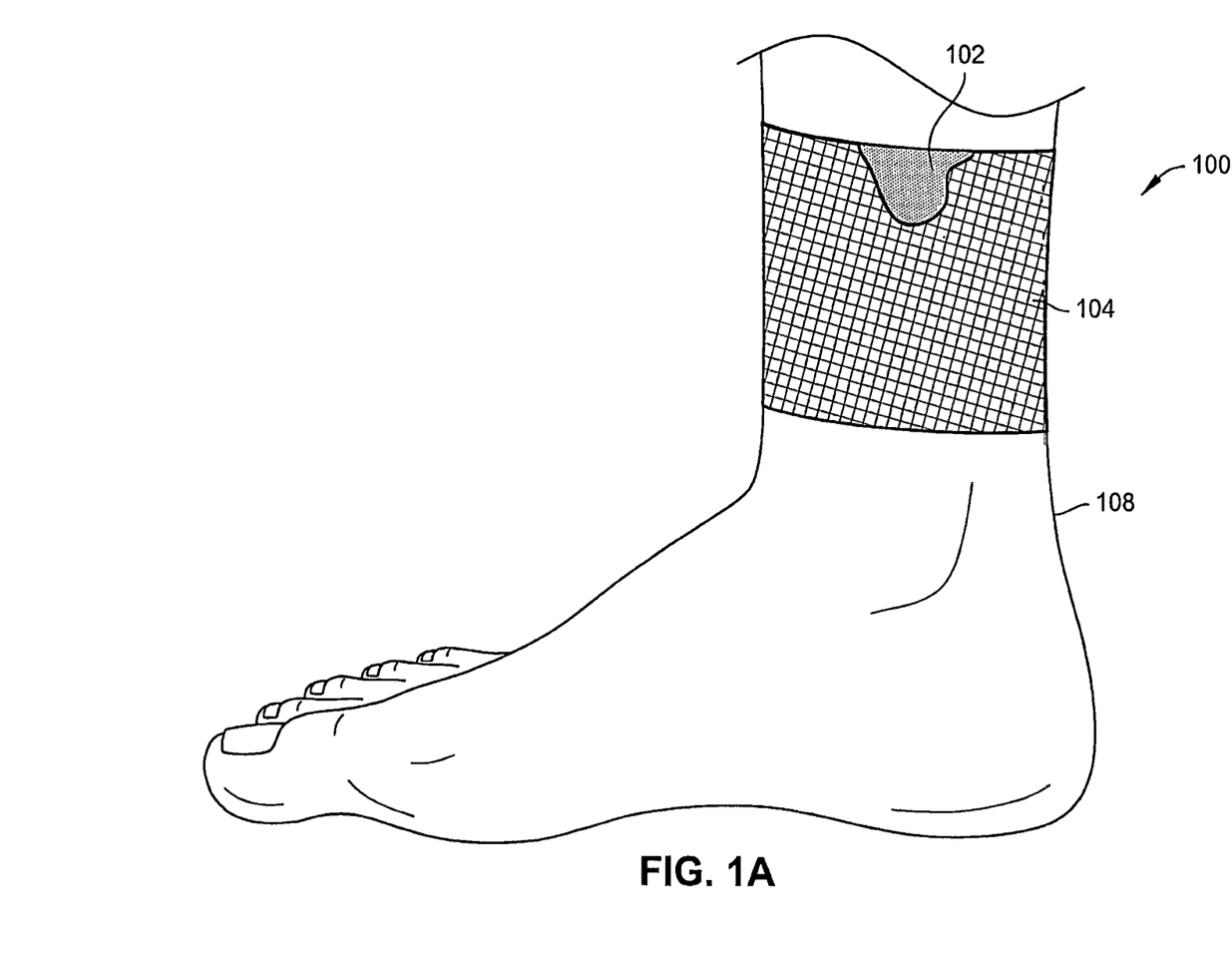
FIG. 1A is an environmental illustration of a wound dressing kit in accordance with embodiments of the present disclosure.
Figure 1B:
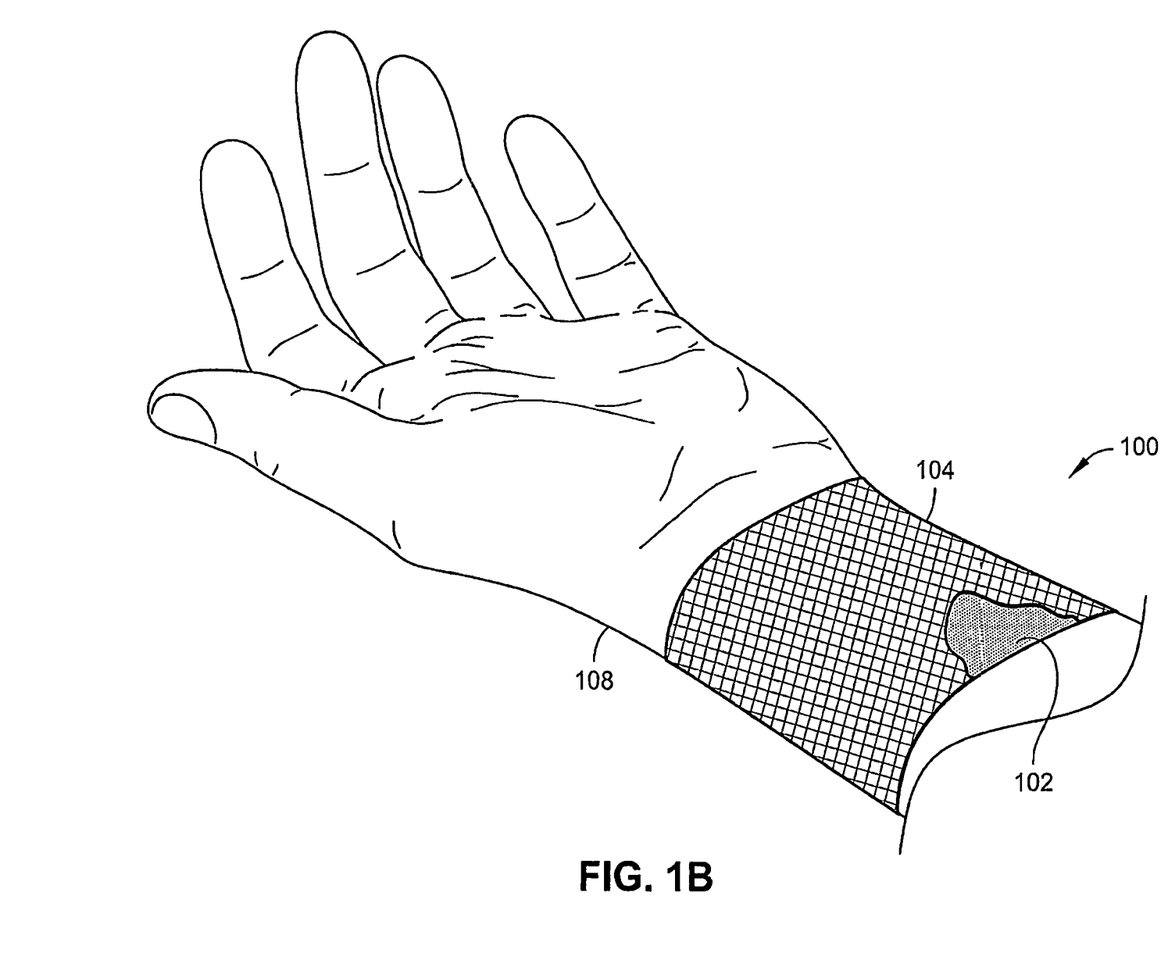
FIG. 1B is another environmental illustration of a wound dressing kit in accordance with embodiments of the present disclosure.
Figure 2:
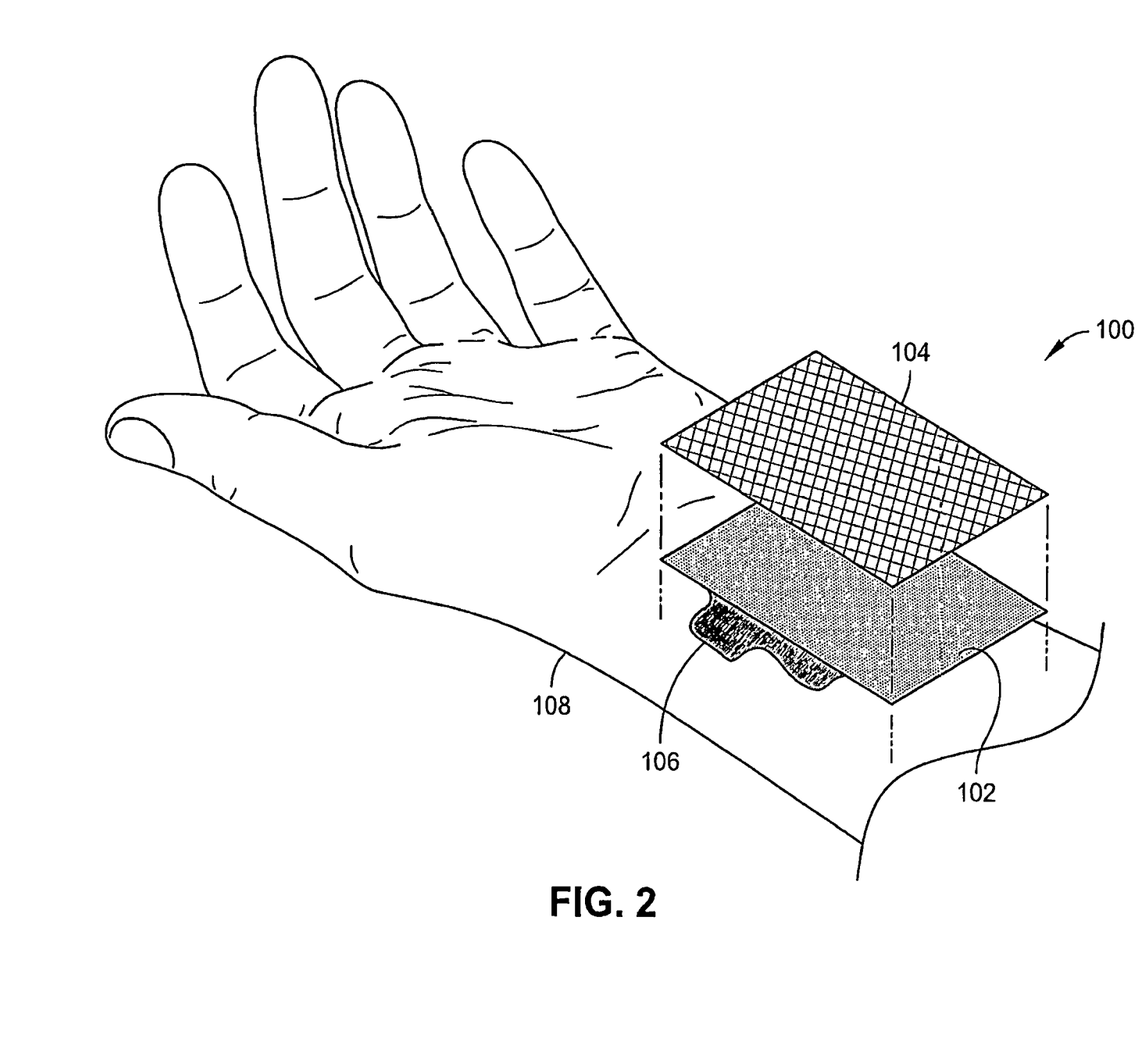
FIG. 2 is an is an exploded environmental illustration of a wound dressing kit, such as the wound dressing kit of FIG. 1, in accordance with embodiments of the present disclosure.
Figure 3:
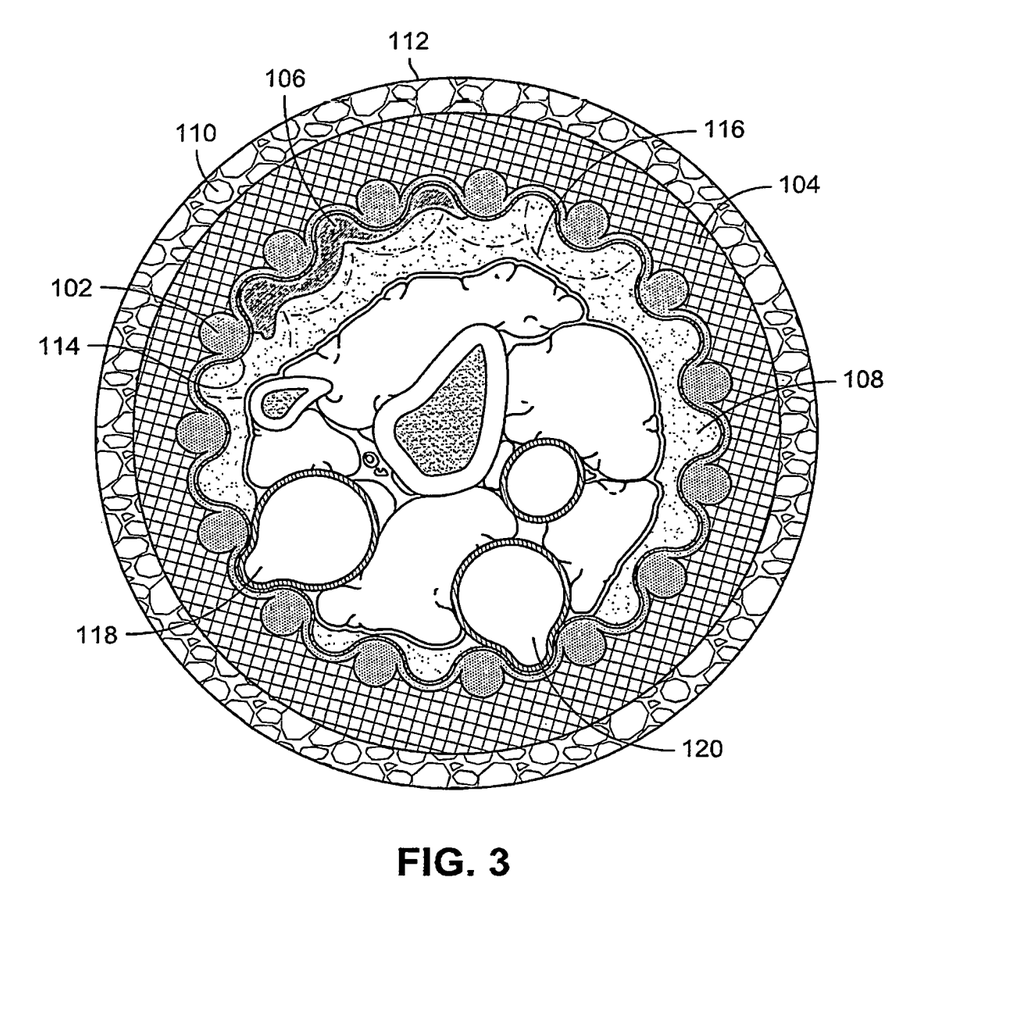
FIG. 3 is a is a schematic illustration of a patient's extremity in cross-section showing the application of a wound dressing kit, such as the wound dressing kit of FIG. 1, in accordance with embodiments of the present disclosure.

The longitudinal wales 202 in the fabric 204 of the present disclosure tends to theraform the skin, creating skin furrows 114 or "cornrows," as noted above (e.g., as described with reference to FIG. 3). In specific embodiments, the furrows may reach a maximum depth of 1.5 to 2.0 times the radius of the longitudinal wale 202. The longitudinal wale 202 "presses in" and forms the furrows in the skin. These furrows 114 can provide significant benefits to the patient. The secondary or lateral elastomeric threads 204 transmit tension/compressive forces to the longitudinal wales 202. The longitudinal wales 202 are thereby "stented" in place by the skin over a given small surface of the wound surface or surrounding skin. The longitudinal wales 202 thus focus compressive force on a small area of the wound surface or surrounding skin. Elastic compression presses the longitudinal wale 202 into the skin and the furrows form in the skin. The convex cross section of the longitudinal wale 202 can act to focus compressive force somewhat like the point of a nail, focusing the energy of a hammer blow onto a tiny surface, creating infinite pressure that drives the nail to pass through, for example, solid oak. Similarly, the wound surface or surrounding skin in the furrow 114 beneath the convex cross section of the longitudinal wale 202 experiences physiologically significant pressure. In some embodiments, the fuzzy outer surface of the wale 202 may also substantially stent and protect the wound surface or skin in immediate contact with the fuzzy surface, creating a fuzzy skin nexus, while applying compression to the wound surface or skin in contact with the fuzzy wale. Thus, when worn, a surface of the wound or the surrounding skin is in contact with a fuzzy skin nexus, and the fuzzy wale skin nexus applies a force of compression to the wound surface and the surrounding skin.

As described above, the secondary elastomeric threads 204 provide only the force of tension between wales 202. The secondary elastomeric threads 204, for the most part, are not in functional contact with the skin. In specific embodiments, when in a state of tension, the secondary elastomeric threads 204 provide a skin surface geography with a ratio of compressed skin surface to substantially uncompressed skin surface of about one to five between adjacent longitudinal wales 202. As described above, the force of tension created by the elastomeric threads 204 causes the longitudinal wales 202 to form furrows 114 in the surface of the wound 106 and the surrounding skin that act as a biological stent. Also, under the force of elastomeric thread tension, the longitudinal wale 202 forming a longitudinal furrow 114 in the skin tends to prevent relative movement of each longitudinal wale with respect to the skin.

The longitudinal wales 202 and elastomeric threads cooperate to create a tensegrity structure. The longitudinal wales 202 stretch the connected secondary spandex elastomeric threads 204. The secondary elastomeric threads 204 are substantially under only the force of tension and interact with the longitudinal wales 202 which are substantially under only the force of compression. This tensegrity structure, comprising a plurality of longitudinal wales 202, fixed in skin cornrow furrows 114, under the force of compression, and secondary elastomeric threads 204 under only the force of tension, translates limb motion into changes in the length of the elastomeric components. Changes in elastomeric thread 204 length changes the compression delivered to the skin via longitudinal wales 202 resting in skin furrows. Limb motion changes in the pressure of compression evidenced by the stented skin in cornrow furrows 114. Resulting pressure changes in the sub cutaneous fat beneath the skin caused by motion of the wearer drives lymphatic pumping of lymph fluid, driving the movement of fluid from the wound 106.

As described above, compression garments 102 formed from the fabric 200 create a "fuzzy nexus" with only a portion of the surface of the wound 106 and the surrounding skin. In some embodiments, approximately 15% to approximately 30% of the periwound skin and granulating wound surface is under physiologically useful compression. In specific embodiments, approximately one fifth (20%) of the periwound skin and granulating wound surface is under physiologically useful compression. In such embodiments, the furrows 114 form in the 20% portion of the periwound skin and granulating wound surface as a result of the force of compression. Approximately four fifths (80%) of the periwound skin and granulating wound surface between wales 202 remains uncompressed. This theraforming of the skin into furrows 114 and uncompressed areas results in the uncompressed area acting as a sink for venous and lymphatic effluent drainage from the compressed area, and provides uncovered wound surface and surrounding skin surface for evaporation of sweat and radiation of heat. Evaporation of sweat results in a drying effect on the skin, which promotes wound healing and reducing the occurrence of damaged skin that may develop into new wounds. Further, the tension generated on the longitudinal wales 202 by the elastomeric threads 204 can be adjusted to deliver appropriate force to resonate with multiple wound cells (e.g., circulating epithelial cell precursors (CEPS)) and initiate the DNA expression and protein generation necessary for wound closure. In such implementations, the fabric 202 is configured to produce physiological responses similar to those created by negative pressure wound therapy, without the use of vacuum pumps or other devices.

On a microscopic level, the following events occur in the skin beneath the longitudinal wale 202 in the furrow 114: First, the external force delivered by the longitudinal wales 202 creates a hydrostatic pressure gradient which moves lymphatic and venous fluid away from the wound site. The thin-walled lymphatic vessels 118 in the fat beneath the skin are compressed and the lymph fluid in these vessels is pushed/squeezed/wrung out by the external pressure delivered by the longitudinal fuzzy longitudinal wale 202 (e.g., as described with reference to FIG. 3). Skin lymphatic vessels 118 and skin veins 120 have one-way valves. Skin pressure changes in this valved tissue vascular structure produce a venous and a lymphatic "physiologic pump" that moves fluid from the skin and subcutaneous fat, reducing swelling at the wound site 106. Lymph fluid in healthy legs is pumped back to the heart from the feet with increased pressure gradients of 1 to 3 centimeters of water. Garments or dressings 102 created with the fabric 200 according to the present disclosure deliver a pressure to the sub dermal fat in excess of 3 centimeters of water in a "halo" 116 of pressure that extends out from the skin furrow 114 beneath each longitudinal wale 202 and into the fat below the skin. This halo 116 of pressure, exceeding three centimeters water, extends far into the tissue around the furrow 114. In this deeply penetrating halo 116 of high pressure, lymphatic flow is greatly enhanced.

Second, the thin-walled veins in the fat beneath the longitudinal wales 202 are emptied of their fluid which constitutes deoxygenated blood rich in lactic acid. Veins in the lower extremity may require pressure gradients of 5 to 15 centimeters of water to return fluid toward the heart. Garments or dressings 102 created with the fabric 200 according to the present disclosure may deliver pressure in excess of 15 centimeters of water in a halo 116 of high pressure around the longitudinal wale 202/skin furrow 114. The cells beneath the longitudinal wale 202 in the zone of pressure above 15 cm of water experience the following: perfusion by arterial blood in the capillaries; pressurized arterial blood is the only fluid that can enter the 116 of >15 centimeter/water tissue pressure. This halo 116 of >15 centimeter pressure causes rapid out flow of venous blood and lymphatic fluid, and causes elevated oxygen tension in the tissues. The halo 116 of >15 centimeter pressure penetrates the fat effectively because the compressive energy is focused by the longitudinal wale 202 stent and the furrowing effect 114. The present disclosure focuses this pressure deep below the skin and delivers pressure that may result in the skin seeing increased tissue oxygenation. For example, the tissue oxygen tension (PaO2) increases from approximately 30 to 38 Torr in venous stasis disease to 80 to 101 Torr when the compression garment 102 is used. Increased oxygen beneath the skin furrow 114 leads to cells being able to "repair" themselves, resulting in the healing of skin ulcers and other wounds. Increased tissue oxygenation also increases the effectiveness of white blood cells to control infection, increasing local healing.

Third, the theraforming effect of the furrows 114 created by the longitudinal wales 202 and elastomeric threads 204 under tension increases arterial perfusion. The static force produced by the wales 202 generates tension in underlying arterial blood vessels, creating narrowed lumen diameters and generating shear forces from blood flow in the small arterial and capillary glycocalyx linings. Such nonlaminar small artery blood flow simulates the capillary wall glycocalyx to release nitric oxide, a powerful vasodilator. Arterial perfusion to the wound surface and surrounding skin beneath the compression garment 102 is significantly increased, sometimes >50%. Increased arterial perfusion prevents a tourniquet effect and increases wound healing.

Third, the static force delivered to the wound surface by the longitudinal wales 202 down regulates tissue levels of certain enzymes. For example, the static force delivered to the wound surface down regulates tissue levels of matrix metalloproteinases (MEMPs) that are released by the host organism to breakdown the hyaline matrix between cells. One example, MMP9 is generally upregulated under normal wound conditions to levels that disrupt healing. The static force delivered by the longitudinal wales 202 can down-regulate the production of MMP9 and other MMPs in the white blood cells of the skin and subcutaneous fat to facilitate wound healing.

The spaces between the longitudinal wales 202 can provide several benefits to wound healing. First, the spaces between the longitudinal wales 202 allow for evaporation of perspiration. Sweat evaporation can reduce the occurrence of periwound maceration, which reduces the incidence of skin shear injuries and bacterial or fungal infections.

Second, the spaces between longitudinal wales 202 allow for the radiation of body heat. Garments or dressings 102 produced with the fabric 202 according to the present disclosure remain cool and comfortable to wear in warm environments. Further, wound dressing kits the include a compression garment 102 layered with a porous dressing layer (e.g., fenestrated dressing layer 104), as described herein, remain breathable and comfortable to wear. Comfort enhances patient compliance.

Third, the spaces between the longitudinal wales 202 allow for the longitudinal wales 202 to press into the skin creating the previously discussed skin furrows 114. The skin between the furrows is in a zone of no pressure. In the no pressure zone, the lymphatic and the venous vessels remain open. Lymphatic flow and venous flow can continue uninhibited toward the heart in the no pressure zone. Garments or dressings 102 produced with the fabric 200 according to the present disclosure do not create a blockage of lymphatic and venous return to the heart (e.g., tourniquet effect). Such a tourniquet effect may impair wound healing and/or result in other pathological conditions.

Fourth, the spaces between the longitudinal wales 202 allow for non-compressed skin between the longitudinal wales 202 and skin furrows 114. This non-compressed skin allows the longitudinal wales 202 to focus a halo 116 of tissue compressive pressure deep into the fat below wound site and the surrounding skin. The no pressure zone enables the halo 116 of physiologically significant tissue pressure to deeply penetrate the fat beneath the wound site and the surrounding skin. Deep penetration encourages rapid tissue healing and rapid resolution of edema at the wound site.

Fifth, when a garment or dressing 102 produced with the fabric 200 according to the present disclosure is removed for dressing changes, bathing, or otherwise replaced, the skin furrows 114 and the non-compressed skin in the no pressure zones are rearranged. This routine change in the location of the skin furrows 114 delivers therapeutic tissue compressive pressure to essentially all of the cells in the covered area roughly about 40% of the time. Thus, all of the cells in the wound surface, the periwound skin, the surrounding skin, and the fat tissue receive the benefit of high tissue pressures delivered in the halos 116 that penetrate deeply beneath the longitudinal wales 202.

Sixth, the theraforming of the skin generated by garments or dressings 102 produced with the fabric 200 reduces the function of fibroblasts and post-burn collagen. This results in decreased formation of scar tissue and a more cosmetic burn or wound skin surface.

Seventh, the spaces between the longitudinal wales 202 provide a significant portion of uncovered wound granulation tissue. With as much as 80% of the wound uncovered, additional contact dressings delivering different therapeutic modalities, such as the fenestrated dressing layer 104 described herein, can share intimate contact with a portion of the wound surface granulation tissue. Accordingly, multiple dressing modalities can simultaneously deliver therapy to the surface of the wound 106.

The secondary or lateral elastomeric threads 204 can provide several benefits to wound healing. First, as described above the lateral elastomeric threads 204 are (physiologically) not in contact with the skin. In some instances, the plurality of secondary transverse elastomeric threads 204 are formed with an amount of space between at least two of plurality of secondary transverse elastomeric threads 204 adequate to provide evaporation of perspiration and radiation of body heat. Thus, the lateral threads 204 may not prevent evaporation of perspiration, or trap body heat.

Second, the lateral threads 204 are not tightly woven in the fabric 200. The lateral elastomeric threads 204 give or stretch easily. This easy stretching makes garments or dressings 102 produced with the fabric 200 of the present disclosure easy to put on and easy to remove. This increases patient compliance. Elderly, frail patients with poor vision can remove and replace the compression garment 102 easily by simply pulling it on and off. This ease of use can reduce the need for inpatient wound care or wound clinic visits.

Third, the secondary or lateral elastomeric threads 204 help to prevent the risk of shearing injury to the skin. The fabric 200 of the present disclosure does not cause shearing injury to frail skin during the dangerous periods when compression garments are put on and removed, which can reduce the risk of further injury to the wound area.

Fourth, the lateral secondary threads 204 are fixed in place between the longitudinal wales 202. The fluffy longitudinal wales 202 stent individual skin cells and the longitudinal wales 202 remain more or less stationary or in place during extremity motion. For instance, the plurality of secondary transverse elastomeric threads 204 disposed between at least two of the plurality of substantially parallel primary wales 202 and substantially equally spaced about a length of the plurality of primary wales 202 may lengthen and shorten during extremity motion of a wearer and generate a dynamic change in tension translatable into a compressive force on the plurality of substantially parallel primary wales 202 suitable for acting as a dynamic pump for at least one of a lymphatic vessel 118 or a vein 120 under a region of skin of a wearer (e.g., as described with reference to FIG. 3). Extremity motion may transfer energy to the lateral elastomeric threads 204 as the lateral elastomeric threads 204 are stretched between the longitudinal wales 202. Extremity motion causes the lateral elastomeric threads 204 between the stationary longitudinal wales 202 to shorten and lengthen. This shortening and lengthening of the lateral elastomeric threads 204 generates compressive force on the primary or longitudinal wales 202. This shortening and lengthening of the lateral elastomeric threads 204 generates a dynamic compressive pressure experienced by the skin in furrows beneath the wales 202. This dynamic compressive pressure acts as an engine that translates extremity motion into compressive force and further acts as a dynamic pump for the lymphatic vessels 118 and the small veins 120 under the skin. With extremity motion, therefore, the present disclosure generates a dynamic change in tissue pressure that results in a pumping action in the veins and the lymphatics in the fat beneath the skin, pumping fluid away from the wound 106 and decreasing edema at the wound site. Improved lymphatic function may also decrease inflammatory mediators (e.g., necrotic fat, enzyme contents of spent white blood cells, matrix metalloproteases, endotoxins, and exotoxins from bacteria).

Fifth, the lateral elastomeric threads 204 generate compressive forces that are focused by the longitudinal wales 202, creating flexibility and "give" in the fabric 200. Garments or dressings 102 produced with the fabric 200 of the present disclosure are comfortable to wear because the patient does not experience a "tight sensation." This "comfort factor" results in high patient compliance.

The hydrophobic longitudinal wales 202 and hydrophilic elastomeric threads 204 can provide several benefits to wound healing. First, the hydrophobic wales 202 and hydrophilic elastomeric threads 204 generate a negative hydrostatic force which wicks moisture from exudate away from the wound 106 and skin surface. This drying effect can reduce the occurrence of periwound maceration, and related skin moisture damage and infection. Second, by reducing moisture at the wound surface, less frequent dressing changes may be needed. Third, by preventing further skin damage and pain associated with periwound maceration, more robust compression therapy can be applied to encourage healing.

In some instances, the forming of a plurality of substantially parallel primary wales 202 in a substantially longitudinal formation may further include forming the plurality of substantially parallel primary wales 202 from a material capable of raising the temperature of the wound surface or surrounding region of skin in contact with the plurality of substantially parallel primary wales 202. The forming the plurality of substantially parallel primary wales 202 from a material capable of raising the temperature of the wound surface or surrounding region of skin may further include forming the plurality of substantially parallel primary wales 202 from a material capable of raising the temperature of the wound surface or surrounding region of skin approximately one to three degrees Fahrenheit.

The forming a plurality of secondary transverse elastomeric threads 204 between at least two of the plurality of substantially parallel primary wales 202 and substantially equally spaced about a length of the plurality of primary wales 202 may further include forming the plurality of secondary transverse elastomeric threads 204 from an elastomeric material.

The forming a plurality of secondary transverse elastomeric threads 204 between at least two of the plurality of substantially parallel primary wales 202 and substantially equally spaced about a length of the plurality of primary wales 202 may further include forming an amount of space between at least two of plurality of secondary transverse elastomeric threads 204 adequate to provide evaporation of perspiration and radiation of body heat. The forming a plurality of secondary transverse elastomeric threads 204 between at least two of the plurality of substantially parallel primary wales 202 and substantially equally spaced about a length of the plurality of primary wales 202 may further include forming the plurality of secondary transverse elastomeric threads 204 in a configuration fixing the plurality of secondary transverse elastomeric threads 204 in place between the plurality of substantially parallel primary wales 202. The forming a plurality of secondary transverse elastomeric threads 204 between at least two of the plurality of substantially parallel primary wales 202 and substantially equally spaced about a length of the plurality of primary wales 202 may further include forming the plurality of secondary transverse elastomeric threads 204 between at least two of the plurality of substantially parallel primary wales 202 and substantially equally spaced about a length of the plurality of primary wales 202 from a material configured to lengthen and shorten during extremity motion of a wearer and generate a dynamic compressive pressure translatable into a compressive force on the plurality of substantially parallel primary wales 202. The forming the plurality of secondary transverse elastomeric threads 204 between at least two of the plurality of substantially parallel primary wales 202 and substantially equally spaced about a length of the plurality of primary wales 202 from a material configured to lengthen and shorten during extremity motion of a wearer and generate a dynamic compressive pressure translatable into a compressive force on the plurality of substantially parallel primary wales 202 may further include forming the plurality of secondary transverse elastomeric threads 204 between at least two of the plurality of substantially parallel primary wales 202 and substantially equally spaced about a length of the plurality of primary wales 202 from a material configured to lengthen and shorten during extremity motion of a wearer and generate a dynamic compressive pressure translatable into a compressive force on the plurality of substantially parallel primary wales 202 suitable for acting as a dynamic pump for at least one of a lymphatic vessel 118 or a vein 120 under a wound 106 or surrounding region of skin of a wearer.

The forming a plurality of secondary transverse elastomeric threads 204 between at least two of the plurality of substantially parallel primary wales 202 and substantially equally spaced about a length of the plurality of primary wales 202 may further include forming an amount of space between at least two of the plurality of substantially parallel primary wales 14 adequate to provide a pressure differential between a region of the wound surface or surrounding skin in contact with at least one of the plurality of substantially parallel primary wales 202 and region of the wound surface or surrounding skin covered by the plurality of secondary transverse elastomeric threads 204. The forming an amount of space between at least two of the plurality of substantially parallel primary wales 202 configured to provide a pressure differential between the region of the wound surface or surrounding skin in contact with at least one of the plurality of substantially parallel primary wales 202 and between the region of the wound surface or surrounding skin covered by the plurality of secondary transverse elastomeric threads 202 may further include forming an amount of space between at least two of the plurality of substantially parallel primary wales 202 applying a non-therapeutic amount of pressure to a region of a wearer covered the plurality of secondary transverse elastomeric threads 204. The forming an amount of space between at least two of the plurality of substantially parallel primary wales 202 adequate to provide a pressure differential between the region of the wound surface or surrounding skin in contact with at least one of the plurality of substantially parallel primary wales 202 and the region of the wound surface or surrounding skin covered by the plurality of secondary transverse elastomeric threads 204 may further include forming an amount of space between at least two of the plurality of substantially parallel primary wales 202 adequate to create an amount of tension causing the plurality of substantially parallel primary wales 202 to apply a substantially continuous amount of pressure to a region of a wearer covered by the plurality of substantially parallel primary wales 202.

The forming an amount of space between at least two of the plurality of substantially parallel primary wales 14 adequate to provide an amount of compression causing the plurality of substantially parallel primary wales 14 to apply a substantially continuous amount of pressure to a region of a wearer covered by the plurality of substantially parallel primary wales 14 may further include forming an amount of space between at least two of the plurality of substantially parallel primary wales 14 adequate to provide an amount of tension causing the plurality of substantially parallel primary wales 14 to apply an amount of pressure sufficient to create a skin furrow within a region of a wearer covered by the plurality of substantially parallel primary wales 14.

In some embodiments, the primary (fuzzy) longitudinal wales 202 are approximately 150% thicker than those described above. In further additional embodiments, the primary wales 14 have a diameter ranging from about 1.2 to about 1.7 mm, or from about 2.2 to about 2.5 mm. Larger diameters (e.g., 2.6 mm and above) are also contemplated.

In some embodiments, the compression garment 102 may be formed as a graduated compression garment having elastic tension that delivers compression which gradually decreases from distal to proximal. For instance, the compression garment may deliver higher compression levels at the ankle, when limb is a leg, and may gradually decrease pressure moving proximally toward the groin. Higher compression at the ankle may drive water up the limb proximally toward the heart. Specifically, graduated compression, with physician prescribed compression levels, as measured in millimeters of mercury, may provide increased compressive elastic force at a first (smaller) limb end (an ankle, when the limb is a leg) and gradually decreasing levels of compressive force moving proximally toward a second (larger) limb end (e.g., the groin). For example, the tubular graduated compression garment may deliver a known level of compression, (e.g., about 25 millimeters of mercury), measured with a blood pressure cuff, at the ankle to encourage the return of venous blood and lymphatic fluid in the subcutaneous fat, toward the heart. A single pigmented fiber may be employed within the graduated compression garment to allow for easy orientation of parallel longitudinal fuzzy wales 202 on the long axis of the limb. Additional embodiments are contemplated suitable for other body parts. For instance, a sock-type graduated compression garment may be formed having at least a portion of the sock formed using graduated compression techniques discussed herein.

The graduated tubular compression garment disclosed herein includes a plurality of longitudinal fuzzy wales 202 arranged to form a fabric 200 with a plurality of transverse elastomeric (e.g., spandex) threads 204 under variable tension connecting the adjacent fuzzy longitudinal wales 202. The fabric 200 may be as described in FIG. 4. The graduated tubular compression garment may be formed in such way as to deliver high levels of elastic compression distally on the limb gradually decreasing in elastomeric tension and elastic compression pressure as the limb increases in diameter proximally. The fuzzy longitudinal wales 202 may be under decreasing tension from small diameter to large diameter, to deliver, when on an extremity such as the lower limb, decreasing compression of the subcutaneous fat, distal to proximal.

To deliver high compression distally where the tubular compression garment has a small diameter and low elastic tension proximally where the tubular compression garment has a larger diameter, the tension on the elastomeric yarns is "graduated" in a manner that delivers graduated elastic tension, distal to proximal, that generates graduated compression of the skin and underlying subcutaneous fat. Thus, the graduated tubular compression garment may be formed substantially as a cylindrical or tubular shaped garment and may further include a plurality of substantially parallel longitudinal fuzzy wales 202, that maintain uniform fuzzy warp knitted wale diameters under decreasing, graduated elastic tension, distal to proximal, delivered by a plurality of secondary elastic-type (e.g., spandex) elastomeric threads 204 with gradually decreasing tension while at rest, (not deployed on an extremity), under no distention, in the graduated compression garment or deployed as a graduated compression garment on an extremity. When the graduated tubular compression garment is deployed on a limb, the distance between parallel wales 202 increases slightly as limb diameter increases without deforming the diameter or surface architecture of the fuzzy wales 202 in contact with the skin and underlying subcutaneous fat. The plurality of substantially primary wales 202 and the plurality of secondary elastomeric threads 204, knitted on a warp knitting machine, form the plurality of substantially parallel primary wales 202 that are under continuously decreasing elastic tension, distal to proximal, in a manner to form a garment that has a small distal diameter when employed on a limb distally that gradually enlarges to a larger diameter on the proximal limb. The diameter of the fuzzy wale remains uniform despite differing elastomeric fiber tension. Each of the plurality of substantially parallel primary wales 202 is formed from a material having a fuzzy outer surface that is of uniform diameter while delivering graduated elastic tension.

The presently disclosed graduated compression garment may be specifically formed to focus tension between transverse elastomeric fibers 204 that limits compression of the subcutaneous fat under the wound and surrounding skin at risk to about 20 to 30% of the skin surface. In some embodiments, the compression is limited to about 20% of wound surface. In other embodiments, the compression is limited to about 25% of wound surface. This ratio of compressed subcutaneous fat, under the furrows 114 that form beneath the longitudinal fuzzy wales 202, to non-compressed subcutaneous fat between wales 202, is on a continuum of ratios, 1:5, 1:4 or 1:3, depending on the diameter of the limb and the diameter of the tubular graduated compression garment. As water is compressed from the subcutaneous fat, furrows 114 (or "corn rows") in the subcutaneous fat may result. In furrows 114 in fat under the wales 202, one or more physiological modifications may occur. For instance, excess water (edema fluid) may drain away from the compressed fat via open lymphatic vessels 118 between the furrows escaping into the lymphatic vessels 118 of the leg muscles beneath the superficial subcutaneous fat. Also, as furrows 114 form beneath wales 202, the fat directly below the fuzzy wale/skin nexus at the furrow's edge may experience relatively high levels of compression.

For instance, one millimeter (mm) away from the fuzzy wale skin nexus at the furrows edge, the pressure decreases. Two mm away, the pressure continues to dissipate in the waterlogged fat stewing in deoxygenated venous blood spike with metabolic toxins. Beneath the furrow 114 the elastic compression distributes out into the waterlogged fat in a halo 116 of decreasing pressure, said another way, a pressure gradient radiates out from the fuzzy wales 202 into the subcutaneous fat. Fluid moves from high pressure to low pressure in various ways via mass movement: diffusion of water in the interstitial fat; via lymphatic vessel outflow; and via venules and veins draining from high pressure to low. In this halo of compressed tissue beneath the fuzzy wales 202, fresh arterial capillary blood circulates easily. Blood rich with nutrients and oxygen resuscitates skin cells harmed by the venous hypertension, promoting the healing of venous leg ulcers and other wounds. Further still, stale deoxygenated venous blood with high levels of lactate and other metabolic waste drains away from the compressed fat in small venules and veins, following the pressure gradient generated by fuzzy wales 202 and compression from elastomeric threads 204 under tension.

According to further embodiments, the compression garment 102 may provide decreased bacterial over growth on the skin. In one embodiment, the compression garment may be loaded (e.g., impregnated, doped, coated, etc.) with fibers of one or more Group 11 periodic table transition metals. Such a graduated compression garment having embedded Group 11 periodic table transition metal fibers may also decrease odor when worn. In some instances, the compression garment 102 includes any antimicrobial metal providing a germ and microbial free environment within the garment and treated areas. For instance, the compression garment 102 may be loaded with at least one metallic antimicrobial agent, such as for example a silver, copper, copper oxide, gold, magnesium oxide, aluminum oxide, titanium dioxide, zinc oxide, cobalt, nickel, zirconium, molybdenum, tin, lead and/or other metals, metal oxides, metal ions, metal particles or nanoparticles, and alloys, mixtures, or combinations thereof. Any known methods may be used to impart durable antimicrobial activity to the graduated compression garment provides effective, durable, and long-lasting antimicrobial characteristics for the garment surfaces.

In some embodiments, the fabric 200 may include alternating ones of the plurality of longitudinal wales 202 loaded with alternating antimicrobial metals. For example, the plurality of longitudinal wales 202 can include a first set of longitudinal wales 202A loaded with a first metal, and an alternating second set of longitudinal wales 202B loaded with a second metal (e.g., as described with reference to FIG. 5). In a specific embodiment, the alternating wales 202A, 202B are loaded with antimicrobial metals of different electronegativity. In a specific embodiment, the alternating wales 202A, 202B are coated with two of silver, zinc, and/or copper. The alternating metallic wales 202A, 202B create a simple galvanic battery, producing a weak electrochemical current of electrons on the surface of the wound 106 and the surrounding skin between the metals of differing electronegativity. In some embodiments, the flow of electrons on the wound surface results from a force of approximately 0.5 volts to approximately 2.0 volts generated by wound surface cell sodium pumps. In specific embodiments, the flow of electrons on the wound surface results from a force of approximately 0.9 volts to approximately 1.0 volts generated by wound surface cell sodium pumps. The elastomeric threads 204 can enhance this effect by functioning as a salt bridge recruiting dressing moisture to enable sodium and chloride ions to flow during periods when the wound surface and surrounding skin are dry.

Figure 5:
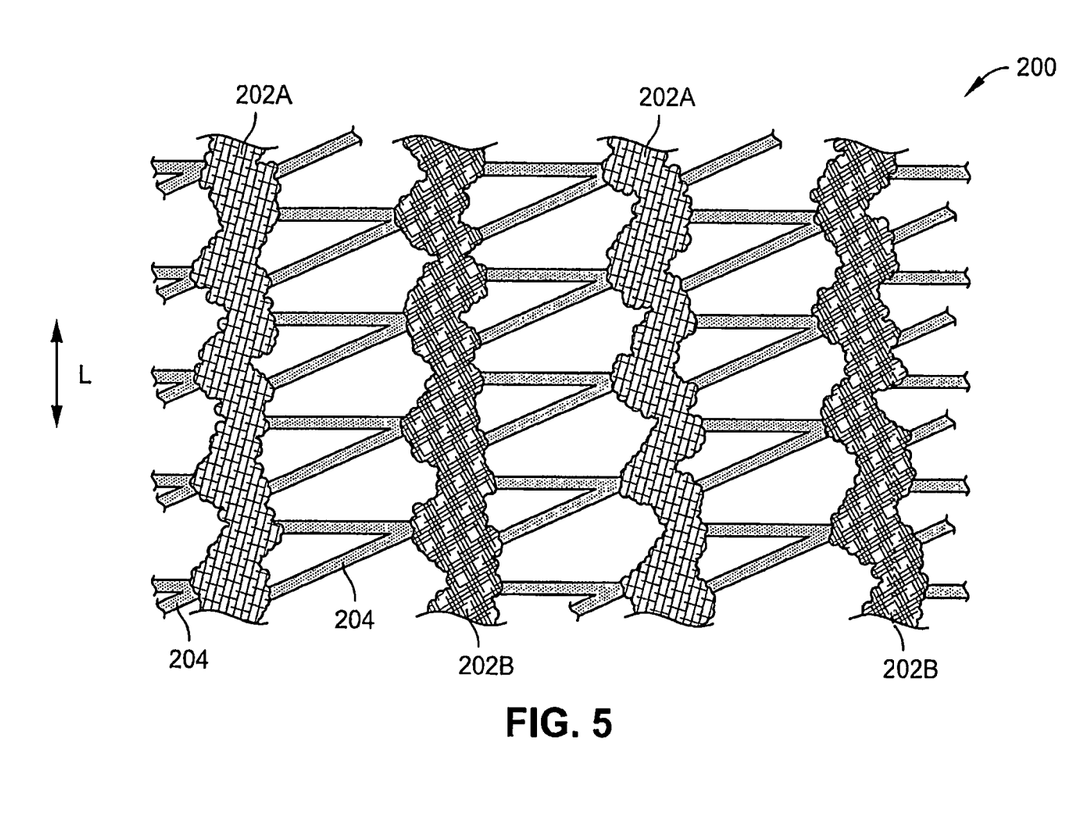
FIG. 5 is another plan view illustrating a fabric constructed in accordance with embodiments of the present disclosure, the fabric shown in a stretched state.

The alternating metallic wales 202A, 202B can provide several benefits to wound healing. First, the current of electrons generated on the surface of the wound 106 and surrounding skin inhibits the growth of bacteria (e.g., biofilm bacteria), decreasing inflammation and inflammatory pain. By reducing pain, more robust compression can be applied to facilitate wound healing. Second, the current of electrons results in galvanic cell taxis, stimulating skin wound surface cells to follow electron currents on the wound surfaces. This is a regenerative physiologic process whereby skin wound surface cells (e.g., epithelial cell precursors from bone marrow totipotent cells and wound edge epithelial skin cells) divide to create daughter cells which migrate along the electron currents flowing from wound edge to wound center to heal the wound.

Figure 6:
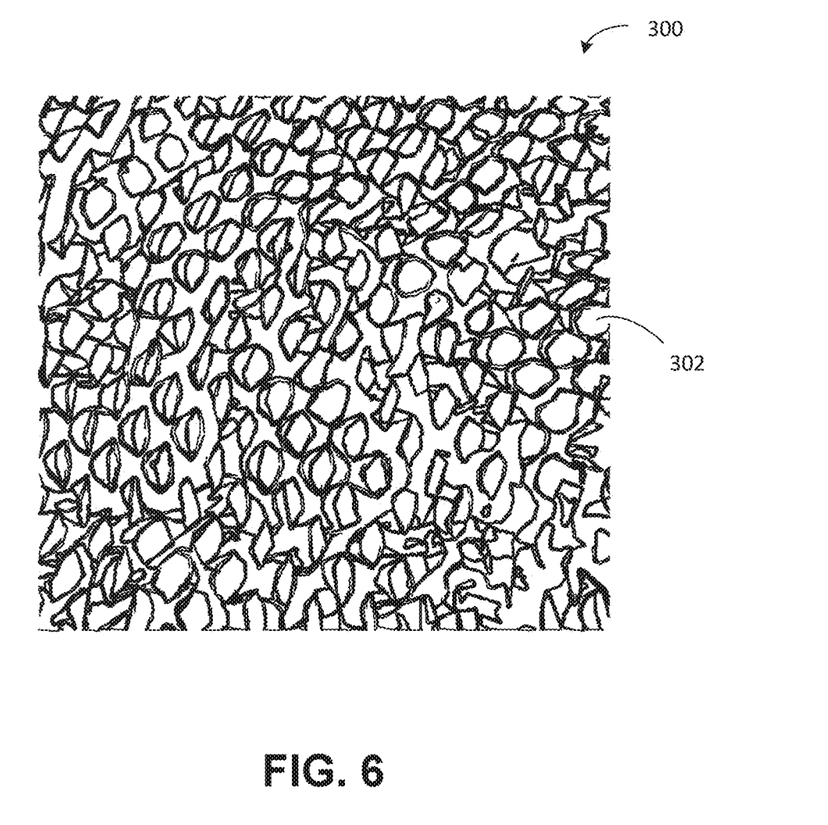
FIG. 6 is another plan view illustrating a fenestrated material constructed in accordance with embodiments of the present disclosure.

As shown in FIG. 6, the fenestrated dressing layer 104 can be formed from any fenestrated material 300 (e.g., any material having perforations or apertures). Such fenestrated materials 300 can pull and/or absorb exudate from the wound surface. In embodiments, the fenestrated material 300 can include activated carbon cloth, a polymer dressing (e.g., a hyper absorbent polymer felt dressing), a polycotton dressing (e.g., a hyper absorbent polycotton felt dressing), knitted cloth (e.g., knitted cloth composed of hydrophobic and/or hydrophilic yarn), other fenestrated/perforated cloths, a bioengineered skin substitute or bioengineered living material (e.g., living bioengineered skin construct, decellularized tissue construct from human or non-human tissue containing tissue growth factors, sacrificial collagen matrices, etc.), open cell foam (e.g., polyurethane foam), a combination thereof, and so forth. In embodiments, the size and orientation of the fenestrations 302 may be selected to interface with the openings of the compression garment 102. For example, the size and shape of the fenestrations 302 may be selected such that the fenestrated material 300 is in direct contact with the wound surface, while still maintaining an open portion of the wound surface.

In some embodiments, the fenestrated material 300 can be impregnated with one or more therapeutic fluids that are compatible with compression therapy. Such therapeutic fluids may include, but are not limited to saline, hypochlorous acid, antibiotics, detergents, anti-odor agents, and so forth. Such therapeutic fluids can enhance be utilized to enhance the therapeutic effects generated by the compression garment 102 and the fenestrated dressing layer 104, and/or provide additional therapeutic effects. In some implementations, the fenestrated dressing layer 104 may be loaded with an antimicrobial metal.

As described above, because the fabric 200 includes spaces between the longitudinal wales 202, the fenestrated material 300 can remain in direct therapeutic contact with the wound surface, even when applied as an outer layer over the compression garment 102. In addition to the therapeutic effects produced by the fenestrated material 300 itself, the fenestrated material 300 forms a textured interface with the compression garment 102 and cooperates with the compression garment 102 to produce additional therapeutic effects. First, the fenestrated material 300 enhances the theraforming effect produced by the longitudinal wales 202 and elastomeric threads 204, enhancing the pressure gradient increasing the flow of lymphatic and venous fluid away from the wound 106 and back towards the heart. Second, the fenestrated material 300 enhances the hydrostatic force generated by the hydrophobic wales 202 and hydrophilic elastomeric threads 204, increasing the movement of exudate away from the wound 106 and skin surface. The porous and absorbent nature of the fenestrated material 300 draws exudate into the material 300 itself and/or into another dressing layer (e.g., dressing layer 110, dressing layer 112), producing an enhanced drying effect. Third, fenestrated materials 300 that are loaded with antimicrobial metal(s) can enhance the regenerative galvanic taxis effect produced by the alternating metallic wales 202A, 202B. Fourth, because the fenestrated material 300 and the compression garment 102 are both breathable, portions of the wound and the surrounding skin remain open, facilitating the evaporation of sweat from exposed skin. The open skin areas also facilitate the use of additional therapeutic modalities (e.g., dressing layer 110, dressing layer 112) and provide those therapeutic modalities with direct wound/skin contact.

In some embodiments, the fenestrated dressing layer 104 may be configured as a fenestrated tubing coupled with an oxygen source (not shown) for providing oxygen therapy to the wound 106. For example, the fenestrated tubing may form an interface with the compression garment 102 such that the fenestrations of the tubing deliver oxygen directly to the wound surface. The fenestrations may be spaced to align with the openings formed by the longitudinal wales 202 and the elastomeric threads 204 (e.g., as described with reference to FIG. 4). In specific embodiments, the fenestrations can be spaced approximately 1 cm apart. By using fenestrated tubing, 100% oxygen can be delivered directly to the wound.

Delivering oxygen therapy directly to the wound 106 can produce several therapeutic effects. First, oxygen therapy can increase the hydroxylation of lysine and proline residues during collagen synthesis, and facilitate the cross-linking and maturation of collagen required for wound healing. Second, adequate tissue oxygenation is necessary for the development of adequate capillary networks. Oxygen therapy can increase the oxygen gradient between the center and periphery of the wound, thus creating a strong angiogenic stimulus. This, along with fibroblastic proliferation, leads to increased neovascularization. Third, oxygen therapy can produce antimicrobial and/or antibacterial effects. Oxygen therapy increases the generation of oxygen free radicals, which oxidize proteins and membrane lipids, damage DNA and inhibit bacterial metabolic functions. Oxygen therapy is particularly effective against anaerobes, which lack superoxide dismutase and facilitates the oxygen-dependent peroxidase system by which leukocytes kill bacteria. Hyperoxia also inhibits clostridial toxin production and improves potency of antibiotics like Fluoroquinolones, Amphotericin B and Aminoglycosides, and other antibiotics which use oxygen for transport across cell membranes. Fourth, oxygen delivered directly to the wound site can produce therapeutic effects similar to those of hyperbaric oxygen therapy without the risks associated with an oxygen-rich environment (e.g., lung collapse, oxygen-induced seizure, fire, etc.).

It is further contemplated that the kit 100 may include one or more additional dressing layers (e.g., as described with reference to FIG. 3). For example, the kit 100 may include a third dressing layer 110 and/or a fourth dressing layer 112. In some embodiments, dressing layer 110 and/or dressing layer 104 may be formed from a fenestrated material (e.g., fenestrated material 300, as described with reference to FIG. 6). In other embodiments, dressing layer 110 and/or dressing layer 112 may be formed from other absorbent and/or elastic materials. In a specific embodiment, dressing layer 110 is formed from an absorbent material (e.g., a loosely woven absorbent material), and dressing layer 112 is formed from an elastic material (e.g., an elastic retention material). In such embodiments, the absorbent material of dressing layer 110, which may or may not be fenestrated, cooperates with the compression garment 102 and the fenestrated dressing layer 104 to further draw exudate away from the wound site. The elastic retention material of dressing layer 112 facilitates holding the layers of the kit 100 in place over the wound 106. Further, because the compression garment 102 and the fenestrated dressing layer 104 cooperate to provide open skin areas, dressing layer 110 and/or dressing layer 112 may have direct contact with the wound site, and the materials of these layers 110, 112 may be selected for their own therapeutic properties.

It is contemplated that the kit 100 may be integrated with and/or utilized with NPWT. For example, the fenestrated dressing layer 104 may be formed from open cell foam or gauze, which can be interfaced and/or connected with a vacuum device. While the compression garments, kits, systems, and methods described herein can be used to produce many of the therapeutic effects of NPWT, there may be implementations in which utilizing the kit 100, for example, in conjunction with NPWT would be beneficial (e.g., difficult wounds or slow-healing wounds).

It is contemplated that the compression garments, kits, systems, and methods described herein may be utilized with all types of wounds including, but not limited to ulcerations (venous ulcers, arterial ulcers, decubitus ulcers, etc.), burns, open wounds (e.g., penetrating wounds, lacerations, etc.), closed wounds (bruises, stasis dermatitis, etc.), and so forth. It is further contemplated that the compression garments, kits, systems, and methods described herein may be utilized with acute and/or chronic wounds.

Although the above descriptions and figures focus primarily on treating the wounds located on the extremities; wounds or other conditions described above that may be located on the torso, head or other area of the body may also be treated using the compression garment 102 according to the present disclosure.

Although the subject matter has been described in language specific to structural features and/or process operations, it is to be understood that the subject matter defined in the appended claims is not necessarily limited to the specific features or acts described above. Rather, the specific features and acts described above are disclosed as example forms of implementing the claims.

What is claimed is:
1. A layered wound dressing kit comprising:
   a compression garment, the compression garment including:
      a plurality of hydrophobic longitudinal wales, the plurality of hydrophobic longitudinal wales including a first set of wales and an alternating second set of wales, the first set of wales loaded with a first metal, and the alternating second set of wales loaded with a second metal different than the first metal, wherein the first set of wales and the alternating second set of wales cooperate to generate an electron current at a wound site; and
      a plurality of hydrophilic transverse elastomeric threads under variable tension, the plurality of hydrophilic transverse elastomeric threads arranged to form a fabric with the plurality of hydrophobic longitudinal wales by connecting adjacent ones of the plurality of hydrophobic longitudinal wales in such way as to deliver elastic compression at the wound site, wherein the plurality of hydrophobic longitudinal wales and the plurality of hydrophilic transverse elastomeric threads cooperate to generate hydrostatic pressure for transporting fluid away from the wound site; and one or more absorbent fenestrated dressing layers configured to form a textured interface with the compression garment and increase movement of the fluid way from the wound site, each of the one or more absorbent fenestrated dressing layers including a plurality of fenestrations, wherein the plurality of fenestrations interface with the plurality of hydrophobic longitudinal wales and the plurality of hydrophilic transverse elastomeric threads such that each of the compression garment and the absorbent fenestrated dressing layer are in direct contact with the wound site, and wherein the one or more absorbent fenestrated dressing layers includes at least one of a polymer felt dressing, a polycotton felt dressing, or an open cell foam dressing.

2. The wound dressing kit of claim 1, wherein the one or more absorbent fenestrated dressing layers includes at least one of an activated carbon cloth or a knitted cloth dressing.

3. The wound dressing kit of claim 1, wherein the fenestrated dressing layers includes at least one of a skin construct or a decellularized tissue construct.

4. The wound dressing kit of claim 1, wherein the one or more absorbent fenestrated dressing layers includes at least a first fenestrated dressing layer and at least a second fenestrated dressing layer.

5. The wound dressing kit of claim 1, wherein the plurality of hydrophobic longitudinal wales and the plurality of hydrophilic transverse elastomeric threads cooperate to deliver elastic compression to a portion of a skin surface at the wound site in a range of 15 percent of the skin surface to 25 percent of the skin surface.

6. A wound dressing kit comprising:
a compression garment, the compression garment including a plurality of hydrophobic longitudinal wales arranged on an interior surface of the compression garment configured to interface with a wound site to form a fabric with a plurality of hydrophilic transverse elastomeric threads under variable tension connecting adjacent ones of the hydrophobic longitudinal wales in such way as to deliver elastic compression at the wound site, wherein the plurality of hydrophobic longitudinal wales and the plurality of hydrophilic transverse elastomeric threads cooperate to generate hydrostatic pressure for transporting fluid away from the wound site, and wherein the plurality of hydrophobic longitudinal wales includes a first set of wales and an alternating second set of wales, the first set of wales loaded with a first metal, and the alternating second set of wales loaded with a second metal different than the first metal, wherein the first set of wales and the alternating second set of wales cooperate to generate an electron current at the wound site; and one or more absorbent fenestrated dressing layers configured to form a textured interface with the compression garment on an outer surface of the compression garment and increase movement of the fluid away from the wound site, each of the one or more absorbent fenestrated dressing layers including a plurality of fenestrations, wherein the plurality of fenestrations interface with the plurality of hydrophobic longitudinal wales and the plurality of hydrophilic transverse elastomeric threads such that each of the compression garment and the absorbent fenestrated dressing layer are in direct contact with the wound site, and wherein the one or more absorbent fenestrated dressing layers includes at least one of a polymer felt dressing, a polycotton felt dressing, or an open cell foam dressing.

7. The wound dressing kit of claim 6, wherein the first metal comprises a first antimicrobial metal.

8. The wound dressing kit of claim 7, wherein the second metal comprises a second antimicrobial metal, the second antimicrobial metal a different antimicrobial metal than the first antimicrobial metal.

9. The wound dressing kit of claim 6, wherein the one or more absorbent fenestrated dressing layers includes at least one of an activated carbon cloth or a knitted cloth dressing.

10. The wound dressing kit of claim 6, wherein the wherein the one or more absorbent fenestrated dressing layers includes at least one of a skin construct or a decellularized tissue construct.

11. The wound dressing kit of claim 6, wherein the plurality of hydrophobic longitudinal wales and the plurality of hydrophilic transverse elastomeric threads cooperate to deliver elastic compression to a portion of a skin surface at the wound site in a range of 15 percent of the skin surface to 25 percent of the skin surface.

12. A wound dressing kit comprising:
a first dressing layer configured to be disposed on an interior surface of the wound dressing kit to interface with a wound site, the first dressing layer including:
a plurality of hydrophobic longitudinal fuzzy wales, the plurality of hydrophobic longitudinal fuzzy wales including a first set of wales and an alternating second set of wales, the first set of wales loaded with a first metal, and the alternating second set of wales loaded with a second metal different than the first metal, wherein the first set of wales and the alternating second set of wales cooperate to generate an electron current at the wound site; and
a plurality of hydrophilic transverse elastomeric threads under variable tension, the plurality of hydrophilic transverse elastomeric threads arranged to form a fabric with the plurality of hydrophobic longitudinal fuzzy wales by connecting the adjacent ones of the plurality of hydrophobic longitudinal fuzzy wales in such way as to deliver elastic compression at the wound site, wherein the plurality of hydrophobic longitudinal fuzzy wales and the plurality of hydrophilic transverse elastomeric threads cooperate to generate hydrostatic pressure that transports fluid away from the wound site; and
a second dressing layer on an outer surface of the first dressing layer, the second dressing layer consisting essentially of an absorbent fenestrated felt dressing, the second dressing layer configured to form a textured interface with the first dressing layer such that each of the first dressing layer and the second dressing layer are in direct contact with the wound site to increase movement of the fluid way from the wound site.

13. The wound dressing kit of claim 12, wherein the first metal comprises a first antimicrobial metal.

14. The wound dressing kit of claim 12, wherein the second metal comprises a second antimicrobial metal, the second antimicrobial metal a different antimicrobial metal than the first antimicrobial metal.

15. The wound dressing kit of claim 12, wherein the plurality of hydrophobic longitudinal fuzzy wales and the plurality of hydrophilic transverse elastomeric threads cooperate to deliver elastic compression to a portion of a skin surface at the wound site in a range of 15 percent of the skin surface to 25 percent of the skin surface.

16. The wound dressing kit of claim 12, wherein the plurality of hydrophobic longitudinal fuzzy wales and the plurality of hydrophilic transverse elastomeric threads cooperate to deliver elastic compression to about 20 percent of a skin surface at the wound site.

17. A method of applying a wound dressing kit to a wound site, comprising:
- introducing a compression garment to a body surface including a wound site, the compression garment including:
  - a first dressing layer configured to be disposed on an interior surface of the compression garment to interface with the wound site, the first dressing layer including:
    - a plurality of hydrophobic longitudinal fuzzy wales, the plurality of hydrophobic longitudinal fuzzy wales including a first set of wales and an alternating second set of wales, the first set of wales loaded with a first metal, and the alternating second set of wales loaded with a second metal different than the first metal, wherein the first set of wales and the alternating second set of wales cooperate to generate an electron current at the wound site, and
    - a plurality of hydrophilic transverse elastomeric threads under variable tension, the plurality of hydrophilic transverse elastomeric threads arranged to form a fabric with the plurality of hydrophobic longitudinal fuzzy wales by connecting the adjacent ones of the plurality of hydrophobic longitudinal fuzzy wales in such way as to deliver elastic compression at the wound site, wherein the plurality of hydrophobic longitudinal fuzzy wales and the plurality of hydrophilic transverse elastomeric threads cooperate to generate hydrostatic pressure that transports fluid away from the wound site, and
  - a second dressing layer on an outer surface of the first dressing layer, the second dressing layer consisting essentially of an absorbent fenestrated felt dressing, the second dressing layer configured to form a textured interface with the first dressing layer such that each of the first dressing layer and the second dressing layer are in direct contact with the wound site to increase movement of the fluid way from the wound site; and
- positioning the dressing layer on the interior surface of the compression garment to interface with the wound site, with an outer surface of the second dressing layer distal the wound site.

18. The method of claim 17, wherein the absorbent fenestrated felt dressing includes an activated carbon cloth.

* * * * *